Figure 1:
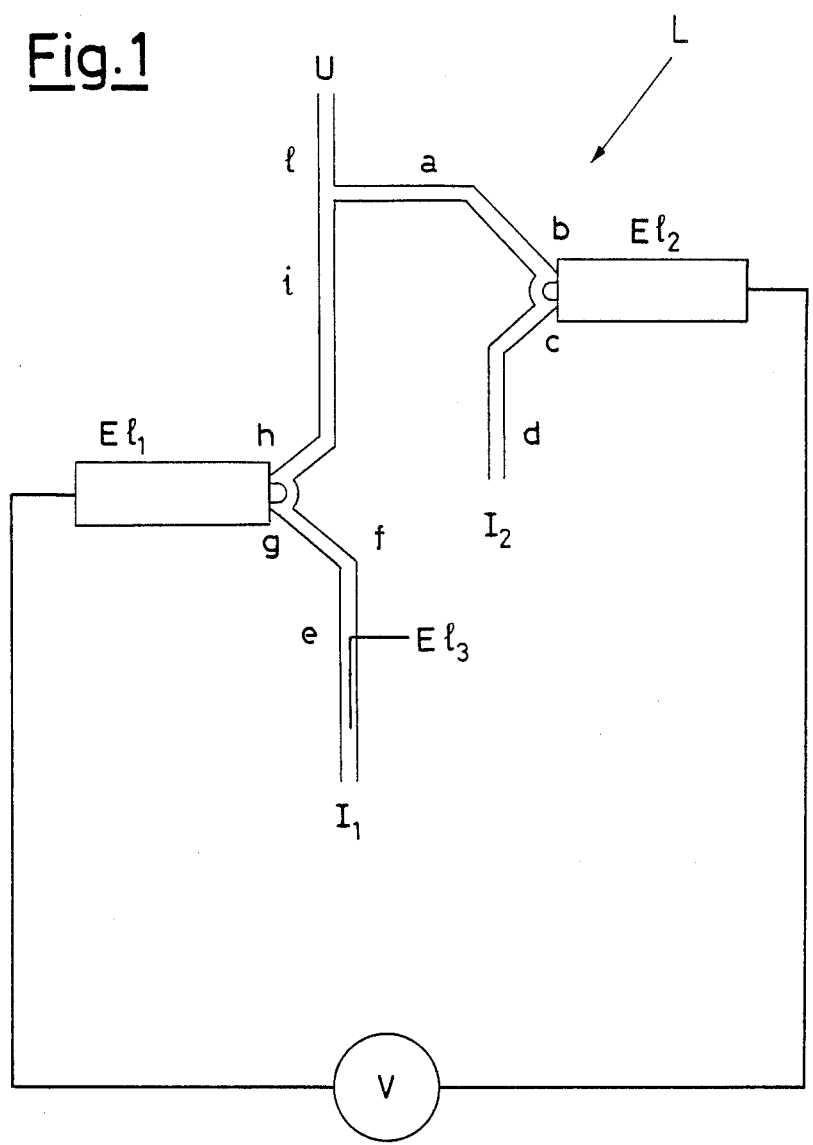

United States Patent [19]
Calzi

[11] Patent Number: 4,966,670
[45] Date of Patent: Oct. 30, 1990

[54] ELECTROCHEMICAL CELL FOR MEASURING IONIC ACTIVITY IN A SOLUTION AND ITS METHOD OF USE

[75] Inventor: Claudio Calzi, Milan, Italy

[73] Assignee: Instrumentation Laboratory SpA, Milan, Italy

[21] Appl. No.: 373,899

[22] Filed: Jun. 29, 1989

[30] Foreign Application Priority Data

Jul. 8, 1988 [IT] Italy ................ 21293 A/88

[51] Int. Cl.$^5$ .......................... G01N 27/416
[52] U.S. Cl. ................... 204/406; 204/409; 204/411; 204/416
[58] Field of Search ............ 204/409, 411, 401, 416, 204/418, 419, 1 T, 406

[56] References Cited

U.S. PATENT DOCUMENTS

| | | | |
|---|---|---|---|
| 3,455,793 | 7/1969 | Buzza et al. | 204/1 T |
| 3,658,679 | 4/1972 | Stansell et al. | 204/409 |
| 3,681,205 | 8/1972 | Ducksbury et al. | 204/409 X |
| 3,718,568 | 2/1973 | Neuwelt | 204/401 |
| 3,839,162 | 10/1974 | Ammer | 204/1 T |
| 3,865,708 | 2/1975 | Light et al. | 204/409 |
| 3,997,420 | 12/1976 | Buzza | 204/411 |
| 4,003,705 | 1/1977 | Buzza et al. | 204/415 X |
| 4,053,381 | 10/1977 | Hamblen et al. | 204/418 X |
| 4,357,143 | 11/1982 | Scott | 204/409 X |
| 4,668,346 | 5/1987 | Entwistle | 204/1 T |
| 4,713,165 | 12/1987 | Conover et al. | 204/403 |

OTHER PUBLICATIONS

Stanley Manahan, Anal. Chem., vol. 42, No. 1, pp. 128–129, (1970).
M. J. D. Brand et al., Anal. Chem., vol. 42, No. 13, pp. 1659–1661, (1970).
M. J. D. Brand et al., "Differential Potentiometry with Ion-Selective Electrodes", Anal. Chem., vol. 42, No. 6, pp. 616–622, (1970).

Primary Examiner—G. L. Kaplan
Attorney, Agent, or Firm—Alan M. Doernberg

[57] ABSTRACT

An electrochemical cell for measuring the activity of one or more ionic species such as pNa, pK, pCa, pNH$_4$, pCl etc. consisting of two sensors selective to the actual ionic species, one of which is used as the reference electrode and the other as the measurement electrode.

The two sensors are chosen preferably identical.

The electrode used as the reference electrode is brought into contact with a solution of known ionic activity and an ionic strength which is greater, equal to or substantially greater than that of the unknown solution to be measured.

The measurement electrode is brought into contact with the unknown solution to be measured, while a third electrode is used purely for instrumental reasons and does not participate in the measurement.

9 Claims, 2 Drawing Sheets

ELECTROCHEMICAL CELL FOR MEASURING IONIC ACTIVITY IN A SOLUTION AND ITS METHOD OF USE

This invention relates to electrochemical apparatus and more particularly to devices for the potentiometric determination of the unknown activity of one or more ionic species of a solution such as pNa, pK, pCa, pNH$_4$, pCl, etc.

For this purpose ion-selective electrodes are usually used, the most common and widespread of which is the pH measurement electrode.

The ion-selective electrode known as the "measurement electrode" is not suitable for this purpose if used alone because the determination of the ionic species presupposes measurement of the potential difference between said electrode and a reference system.

In practice the reference system is a second electrode known as the "reference electrode".

The "reference electrode" is usually a half cell the potential of which is considered fixed, whatever the solution with which it is brought into contact.

It generally consists of a calomel or similar electrode. Both the measurement electrode and reference electrode are immersed in the solution to be measured.

The electromotive force, known as E, which is obtained under these conditions can be represented schematically in the following manner:
measurement electrode | solution X ⋮⋮ salt bridge(KCl) ⋮⋮ reference electrode, where the dotted lines indicate the sites of the liquid junctions.

The electromotive force E is governed by the Nernst equation:

$$E = \frac{2.3026\, RT}{nF} \log A \quad (1)$$

in which:
E is the measured potential
A is the activity of the ion to be measured $$\frac{2.3026\, RT}{nF}$$

is the proportionality factor.

To be of practical use the cell composed of the said reference and measurement electrodes must be standardized. In other words the potential generated in the presence of a solution of known ion activity must be known.

The practical measurement is obtained using the following formula:

$$\log A = \log A(S) + \frac{E - E_s}{2.3026\, RT/nF} \quad (2)$$

where A(S) is the solution of known activity, E is the measured potential and Es is the potential generated in the presence of the known solution.

This is valid if the liquid junction potentials do not change when solution X is used instead of the known solution.

For this reason, precautions are taken to minimize the liquid junction potential and make it as stable as possible by saturating the salt bridge, which is usually done by increasing the molarity of the KCl solution, using an electrolyte consisting of a salt of equivalent cation and anion mobility.

The invention consists of the appropriate use of two ion-selective sensors, without using conventional reference electrodes.

The two sensors can be identical, in which case one of the sensors is used as the reference electrode and the other as the measurement electrode.

The electrode used as the reference electrode is placed in contact with a solution of predetermined ionic activity (S), whereas the measurement electrode is placed in contact with the unknown solution (X).

Thus the present invention provides an electrochemical cell able to measure the unknown specific ionic activity of a solution by using at least two ion-selective electrodes, of which one is used as the reference sensor in contact with a solution of ionic activity which is standardized within a predetermined range, and the other is used as the measurement sensor; the known solution and the unknown solution being brought into mutual ionic contact, the known solution having an ionic strength which is at least equal to and in practice substantially greater than that of the unknown solution in order to determine an electrolytic short circuit with the unknown solution, there being also provided in the cell at least a third electrode the purpose of which is simply to act as an electrical conductor for practical measurement purposes.

Figure 2:
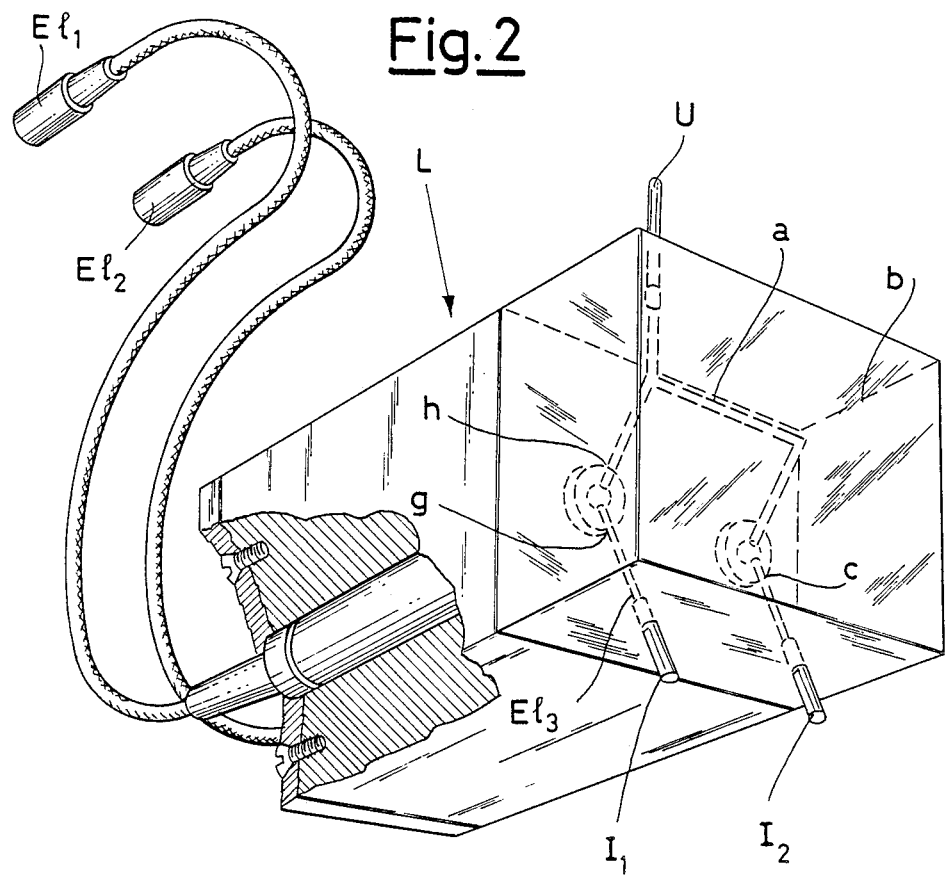
Figure 3:
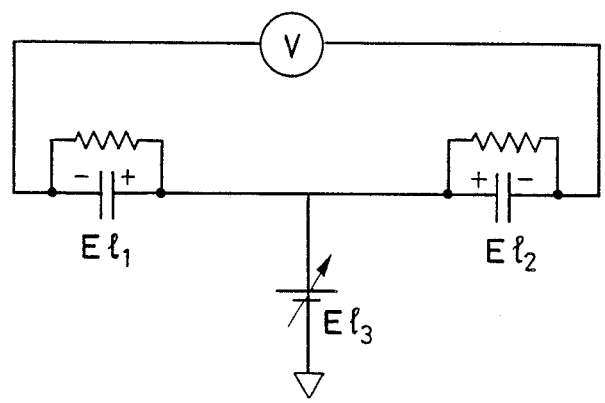

The electrochemical cell according to the present invention is illustrated by way of non-limiting example on the accompanying drawings which show a preferred embodiment thereof, FIG. 1 being a diagrammatic view,
FIG. 2 being a perspective view and
FIG. 3 representing the equivalent simplified electrical circuit of the measurement cell.

The solution S should have a known ionic activity for the particular species for which the (reference) electrode is markedly selective, and other "neutral" salts or indifferent electrolytes are added to it such as to increase its final ionic strength (experimental ranges 0.3–1.5) to the level at which it resembles a "salt bridge" constituting an electrolytic short circuit and thus minimizing the junction potential in the contingent situation.

The two solutions (S) and (X) are placed in contact to produce ionic connection therebetween.

The ionic contact zone, which is the seat of diffusion between two fluids, is preferably located at a sufficient distance from the measurement chamber so as not to alter the ionic concentrations in proximity to the sensors, for the time required for the measurement.

As can be seen from the drawings (FIG. 1), an electrochemical cell L is provided in which there are connected two ion-selective electrodes selective towards the same ionic species, El$_1$, and El$_2$, and a third metal electrode El$_3$ which is required only for the operation of the electronic measuring instrument, not shown, for measuring the electromotive force or potential V across the two electrodes.

The cell L comprises two inlets I$_1$, and I$_2$ and one outlet U which represent the fluid path of the system. If the measurement cell L is completely filled (inlets I$_1$, and I$_2$, outlet U) with a solution having a certain ionic activity compatible with the electrodes used, the measured potential difference V will be zero if the electrodes El$_1$, and El$_2$ are identical in terms of potential, asymmetry and internal electrolyte.

Each of said electrodes, each of which forms one electrochemical half cell, will develop an equal electromotive force with respect to the solution introduced into the cell, so that a differential measurement will show a zero value of the potential V.

Any deviations from zero in practice can be compensated by adjusting to zero the measuring apparatus to which the cell L is connected.

If a solution having a known ionic activity S is introduced into the cell the result will always be zero.

Starting from this condition a solution of unknown ionic activity X is introduced into the measuring cell L so that it only extends from the fluid inlet I, and along the points, f, g, h, i and as far as the outlet U, whereas the fluid path extending along the points $I_2$, d, c, b, a is still filled with the solutions S. V will then assume a value which is no longer zero but is proportional to the ionic concentration difference between the solutions S and X in accordance with the stated Nernst law.

In the immediate proximity of the point 1 diffusion takes place between the two sustances S and X, with the consequent ionic contact necessary for measurement.

From FIG. 3, which represents the equivalent electrical circuit of the cell L, it is apparent that the variable potential which develops at the electrode $El_3$ does not participate in the measurement of V.

The measured potential difference V can be represented in the following manner:

electrode 1 | solution X ░░ solution S | electrode 2

From this representation, it is clear that the electrode $El_3$ does not participate in the measurement. This electrode is in theory not required, but its presence is dictated by practical aspects relating to the measuring, apparatus. It represents the seat of currents (of the order of between some tens of femto-amperes and a few pico-amperes) circulating from the measuring apparatus, through the measurement electrodes $El_2$, $El_1$, the solutions S, X and as far as the electrode $El_3$ itself.

The potential differences (conventionally referred to as of common mode) either between $El_1$ and $El_3$, or between $El_2$ and $El_3$, or both, are not sensed by the measuring apparatus.

Having stated this, the interface between the solutions S and X, i.e. the liquid junction potential, merits specific consideration for the purposes of the electrochemical system concerned.

If certain precautions are used in said cell in terms of the choice of calibration solutions for the unknown solutions, the interliquid potential can be reduced to negligible value.

The optimum conditions are as follows:
(1) The solution S of known activity preferably contains neutral salts or support electrolytes, whose concentration does not affect the potential measured by the electrode $El_2$, in a quantity sufficient to make the overall ionic strength of solution S at least 0.15 (units), and preferably 0.3 to 1.5 (units).
(2) The ionic strength of the electroactive species under examination should typically not exceed 0.16.
(3) The electroactive species under examination in solution X and in the known solution S should have a concentration which is negligible compared to the concentration of the support electrolyte in the known solution S.
(4) The concentration difference between the species under examination and the reference species should not differ by more than two orders of magnitude.

Numerous experimental tests have been carried out with the electrochemical cell according to the invention (FIG. 2).

These have shown the following:
The potential V can be calculated using formula (2) stated in the introduction to this description.

The operation of cell L is limited only if the four aforesaid recommendations are not respected.

The measurement reproducibility of the cell of the invention has been surprisingly good (variations <5/1000 pH).

The speed of response of the sensors in this configuration is very fast (about 10 seconds).

The most evident practical advantage is the elimination of the reference electrode (e.g. Ag/AgCl or calomel in 3M or saturated KCl) and all the drawbacks connected with it.

In the cell L the fluid path must be dimensioned to limit diffusion between the fluids S and X so that an exchange of ionic activity takes place in the measuring chambers defined by the fluid portions b, c, and h, g respectively (FIGS. 1, 2), for the time required for taking the measurement.

The standardization and measurement methods for the electrochemical cell according to the invention do not differ substantially from the current methods for traditional cells.

Specifically, using a typical standardization method the cell L is firstly completely filled with a solution of known activity A (S) and the solution to be measured is then introduced into one half cell.

In practice it may be necessary to also introduce into one half cell a second solution of known activity, different from A (S), to ensure the slope of the straight line on which the electromotive force E is located.

One skilled in the art would appreciate which particular compositions of solution S and S' might be used to ensure (or determine) the slope of the line of activity versus voltage.

As an alternative, a solution of approximate but stable concentration can be used, plus two known substances successively in the other half cell, to obtain two points on the straight line. Taking account of the aforegoing, the case was examined in which $El_1$ and $El_2$ are not selective towards the same species.

The reference electrode $El_2$ is always placed in contact with a solution of known ionic activity for the species towards which it is markedly selective.

It is therefore valid to suppose that its potential against the calibration solution is constant for practical purposes.

The electrode $El_1$ in contact with the solution X develops a potential which is a function of the activity of the solution X for the species towards which $El_1$ is selective. If the interliquid potential is negligible or approximately constant, a potential difference can be measured between $El_1$ and $El_2$ which is proportional to X plus a constant, in accordance with the Nernst equation.

The usefulness of this application is easily apparent to the expert of the art and easily allows applications to be imagined in which $El_1$, $El_11$, $El_12$, $El_1n$ can exist, each specific for a specific ionic species, while $El_2$ performs its reference function.

It will be apparent to the expert of the art that the electrochemical cell according to the invention can find many applications in the industrial field, in analytical chemistry and in particular in clinical chemistry.

I claim:

1. An electrochemical cell for measuring the unknown specific ionic activity of a solution comprising at least two ion-selective electrodes, a first ion-selective electrode being in contact with a known solution of ionic activity which is standardized within a predetermined range, and a second ion-selective electrode being a measurement sensor; the known solution and an unknown solution being in mutual contact, the known solution having an ionic strength which is at least equal to that of the unknown solution, the electrochemical cell further comprising means for determining the potential of an electrolytic short circuit between the first ion-selective electrode in contact with the known solution and the second ion-selective electrode in contact with the unknown solution, the electrochemical cell also comprising a third electrode connected to remove current from the electrochemical cell.

2. An electrochemical cell as claimed in claim 1 wherein the two ion-selective electrodes are selective to the same ionic species.

3. An electrochemical cell as claimed in claim 2 wherein the two ion-selective electrodes selective to the same ionic species are identical to each other.

4. An electrochemical cell as claimed in claim 1 further comprising two separate inlets and one common outlet for the two solutions, the known solution and the unknown solution coming into mutual ionic contact in a circumscribed zone in proximity to the outlet but sufficiently far from measurement chambers in which the first and second ion-selective electrodes are housed that disturbances due to diffusion between the known and unknown solutions during the time required for the measurement by the means for determining do not affect the measurement, with the known and unknown solutions being stationary during the measurement.

5. An electrochemical cell as claimed in claim 4 wherein the first ion-selective electrode is selective toward a species different from the species to which the second ion-selective electrode is selective, the first ion-selective electrode being in contact with a reference solution in which the ionic activity of the species for which the first ion-selective electrode is specific is known and constant.

6. A standardization and measurement method comprising filling from both inlets to the common outlet the electrochemical cell claimed in claim 4 with a solution of known activity, making a first measurement with the measuring means, then introducing into one half of said cell from the second inlet to the common outlet a first unknown solution, and then making a second measurement with the measurement means.

7. The standardization and measurement method of claim 6 further comprising then introducing from the second inlet to the common outlet a second unknown solution to displace the first unknown solution from the cell and then making a third measurement with the measurement means.

8. The standardization and measurement method of claim 7 wherein the first and second ion-selective electrodes are each selective toward the same ionic species.

9. The standardization and measurement method of claim 7 wherein the first ion-selective electrode is selective toward a species different from the species to which the second ion-selective electrode is selective, the first ion-selective electrode being in contact with a reference solution in which the ionic activity of the species for which the first ion-selective electrode is specific is known and constant.

* * * * *